(12) United States Patent
Sikavitsas et al.

(10) Patent No.: US 11,045,584 B2
(45) Date of Patent: Jun. 29, 2021

(54) PRODUCING BONE TISSUE ENGINEERED CONSTRUCTS

(71) Applicant: The Board of Regents of the University of Oklahoma, Norman, OK (US)

(72) Inventors: Vassilios Sikavitsas, Norman, OK (US); Aaron D. Simmons, Fort Worth, TX (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 499 days.

(21) Appl. No.: 16/102,306

(22) Filed: Aug. 13, 2018

(65) Prior Publication Data

US 2019/0054210 A1 Feb. 21, 2019

Related U.S. Application Data

(60) Provisional application No. 62/545,820, filed on Aug. 15, 2017.

(51) Int. Cl.
| | |
|---|---|
| *A61L 27/38* | (2006.01) |
| *C12N 5/077* | (2010.01) |
| *A61L 27/18* | (2006.01) |
| *A61L 27/56* | (2006.01) |
| *G01N 33/50* | (2006.01) |
| *C12M 1/00* | (2006.01) |
| *C12M 3/00* | (2006.01) |
| *C12M 1/12* | (2006.01) |

(52) U.S. Cl.
CPC ........ *A61L 27/3821* (2013.01); *A61L 27/18* (2013.01); *A61L 27/3847* (2013.01); *A61L 27/3895* (2013.01); *A61L 27/56* (2013.01); *C12M 21/08* (2013.01); *C12M 25/14* (2013.01); *C12M 29/10* (2013.01); *C12N 5/0654* (2013.01); *G01N 33/5026* (2013.01); *C12N 2506/1346* (2013.01); *C12N 2513/00* (2013.01); *C12N 2521/00* (2013.01); *C12N 2533/40* (2013.01)

(58) Field of Classification Search
None
See application file for complete search history.

(56) References Cited

U.S. PATENT DOCUMENTS

| | | | |
|---|---|---|---|
| 2011/0229970 A1* | 9/2011 | Ma | C12N 5/0654 435/455 |
| 2012/0035742 A1* | 2/2012 | Vunjak-Novakovic | A61F 2/28 623/23.61 |

OTHER PUBLICATIONS

Janssen et al, Biomaterials, 2006, 27: 315-323. (Year: 2006).*
Pattappa et al, Journal of Cellular Physiology, 2011, 226:2562-2570 (Year: 2011).*
Simmons et al, Biosensors and Bioelectronics, 2017, 90: 443-449 (epub date: Sep. 30, 2016). (Year: 2017).*

* cited by examiner

*Primary Examiner* — Allison M Fox
(74) *Attorney, Agent, or Firm* — Hall Estill Law Firm (57) ABSTRACT

A process for producing a bone construct, including the steps of providing a perfusion bioreactor having an inlet and an outlet; providing the perfusion bioreactor with a seeded scaffold comprising a porous scaffold seeded with mesenchymal stem cells; continuously perfusing the seeded scaffold with an osteogenic induction (differentiation) media; measuring dissolved oxygen content of the osteogenic induction media at the inlet and at the outlet to determine an oxygen uptake rate (OUR) for the seeded scaffold; measuring glucose content of the osteogenic induction media to determine a glucose consumption rate (GCR) for the seeded scaffold; and removing the seeded scaffold from the perfusion reactor as a bone construct after the ratio of the OUR to the GCR (OUR/GCR) has been determined to exceed a predetermined threshold OUR/GCR value.

16 Claims, 6 Drawing Sheets

PRODUCING BONE TISSUE ENGINEERED CONSTRUCTS

CROSS REFERENCE TO RELATED APPLICATIONS

The present application claims priority under 35 U.S.C. § 119(e) to U.S. Ser. No. 62/545,820, filed Aug. 15, 2017, the entirety of which is hereby expressly incorporated by reference herein.

BACKGROUND

Bone tissue defects result in the need for more than two million bone graft interventions worldwide annually (with over 500,000 of these being required in the US alone, at a cost of over $2.5 billion). As daunting as these figures appear they are expected to double within the next several years, exacerbated by an increasingly aged and obese population. Common defects requiring surgical intervention span from simple fractures (suffering from non-union or delayed-union complications) to mass resection of bone tissue as a result of malignant tumor formation. Furthermore, bone grafts are often implemented alongside implanted devices, as a means to aid in their incorporation and mitigate the risk of immune rejection thereof. Such high demand, coupled with the low supply and complications associated with traditional graft sources necessitate the need for alternative graft sources.

Bone tissue engineering seeks to overcome the shortcomings of current bone graft sources via the production of constructs with enhanced osteogenicity, osteoconductivity, and osteoinductivity all while reducing the risks of graft rejection, disease transmission, and donor site morbidity.

However, as promising as bone tissue engineered grafts have proven in numerous animal models, there currently exist no products on the market for human clinical intervention due to FDA regulatory demands. Perhaps the biggest impediment to securing FDA approval of bone tissue engineered products is the requirement for the development of a robust program of quality control, necessitating sound methods for the real-time, non-destructive monitoring of such grafts in vitro prior to implantation. In fact, this is one of the main funding thrusts of the National Institute of Biomedical Imaging and Bioengineering in the field of tissue engineering.

Limited studies have addressed the concern of construct monitoring, though it is clear this is necessary for the advancement and clinical implementation of bone tissue engineering approaches. Many groups have investigated the use of biosensors for the monitoring of metabolites within cell culture media, though typically only as a means of modelling gradients or comparing responses to treatments. Some groups have gone so far as to predict cellularity from metabolic flux data, though only for non-differentiating cells with stable metabolism. A method in which cellularity and maturation (defined as differentiation and mineralization) of bone tissue constructs could be determined would be a significant advancement in the field.

BRIEF DESCRIPTION OF THE DRAWINGS

Several embodiments of the present disclosure are hereby illustrated in the appended drawings. It is to be noted however, that the appended drawings only illustrate several embodiments and are therefore not intended to be considered limiting of the scope of the present disclosure.

FIG. 4 shows OUR/GCR ratio versus construct maturation. The ratio of OUR to GCR (plotted on the abscissa) vs the traditional bone tissue engineering construct quality markers of calcium deposition (on the primary ordinate; squares) and cellular alkaline phosphatase (ALP) activity (on the secondary ordinate; circles) provided for both reactor groups (MEM=open symbols, Osteo=black symbols). A clear demarcation can be made between low calcium deposition and ALP activity levels corresponding to low ratios of OUR/GCR and high values of these markers corresponding to high values of this ratio. The three data points for each marker (calcium dep. and ALP) on the right half of the graph (exhibiting OUR/GCR>2.0) correspond to late-culture time points for the Osteo reactor (Days 9, 11, and 14). Those data points for early-culture time points for the Osteo reactor as well as all time points for the MEM reactor exhibit OUR/GCR<2.0.

DETAILED DESCRIPTION

An ever-increasing demand for bone grafts necessitates the realization of clinical implementation of bone tissue engineered (BTE) constructs (also referred to herein as bone constructs). However, due to the lack of viable methods for the rigorous monitoring of the status of BTE constructs, the securing of FDA approval continues to be a predominant hurdle to implementation. The present disclosure sets forth, in at least one embodiment, a method for such monitoring based on the shifting metabolism of mesenchymal stem cells (MSCs) as they differentiate into osteoblasts in a BTE construct. The method comprises the real-time, non-destructive monitoring of a BTE construct cultured in vitro, to determine when the construct has matured. The method is based on the utilization of key metabolic rates, oxygen uptake and glucose consumption.

Before further describing various embodiments of the compositions and methods of the present disclosure in more detail by way of exemplary description, examples, and results, it is to be understood that the embodiments of the present disclosure are not limited in application to the specific details of methods and compositions as set forth in the following description. The embodiments of the compositions and methods of the present disclosure are capable of being practiced or carried out in various ways not explicitly described herein. As such, the language used herein is intended to be given the broadest possible scope and meaning; and the embodiments are meant to be exemplary, not exhaustive. Also, it is to be understood that the phraseology and terminology employed herein is for the purpose of description and should not be regarded as limiting unless otherwise indicated as so. Moreover, in the following detailed description, numerous specific details are set forth in order to provide a more thorough understanding of the disclosure. However, it will be apparent to a person having ordinary skill in the art that the embodiments of the present disclosure may be practiced without these specific details. In other instances, features which are well known to persons of ordinary skill in the art have not been described in detail to avoid unnecessary complication of the description. While the compositions and methods of the present disclosure have been described in terms of particular embodiments, it will be apparent to those of skill in the art that variations may be applied to the compositions and/or methods and in the steps or in the sequence of steps of the method described herein without departing from the concept, spirit, and scope of the inventive concepts as described herein. All such similar substitutes and modifications apparent to those having ordinary skill in the art are deemed to be within the spirit and scope of the inventive concepts as disclosed herein.

All patents, published patent applications, and non-patent publications referenced or mentioned in any portion of the present specification, including U.S. Ser. No. 62/545,820, filed Aug. 15, 2017, are indicative of the level of skill of those skilled in the art to which the present disclosure pertains, and are hereby expressly incorporated by reference in their entirety to the same extent as if the contents of each individual patent or publication was specifically and individually incorporated herein.

Unless otherwise defined herein, scientific and technical terms used in connection with the present disclosure shall have the meanings that are commonly understood by those having ordinary skill in the art. Further, unless otherwise required by context, singular terms shall include pluralities and plural terms shall include the singular.

As utilized in accordance with the methods and compositions of the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or when the alternatives are mutually exclusive, although the disclosure supports a definition that refers to only alternatives and "and/or." The use of the term "at least one" will be understood to include one as well as any quantity more than one, including but not limited to, 2, 3, 4, 5, 6, 7, 8, 9, 10, 15, 20, 30, 40, 50, 100, or any integer inclusive therein. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y and Z" will be understood to include X alone, Y alone, and Z alone, as well as any combination of X, Y and Z.

As used in this specification and claims, the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

Throughout this application, the term "about" is used to indicate that a value includes the inherent variation of error for the composition, the method used to administer the composition, or the variation that exists among the objects, or study subjects. As used herein the qualifiers "about" or "approximately" are intended to include not only the exact value, amount, degree, orientation, or other qualified characteristic or value, but are intended to include some slight variations due to measuring error, manufacturing tolerances, stress exerted on various parts or components, observer error, wear and tear, and combinations thereof, for example. The term "about" or "approximately", where used herein when referring to a measurable value such as an amount, percentage, temporal duration, and the like, is meant to encompass, for example, variations of ±20% or ±10%, or ±5%, or ±1%, or ±0.1% from the specified value, as such variations are appropriate to perform the disclosed methods and as understood by persons having ordinary skill in the art. As used herein, the term "substantially" means that the subsequently described event or circumstance completely occurs or that the subsequently described event or circumstance occurs to a great extent or degree. For example, the term "substantially" means that the subsequently described event or circumstance occurs at least 90% of the time, or at least 95% of the time, or at least 98% of the time.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

As used herein, all numerical values or ranges include fractions of the values and integers within such ranges and fractions of the integers within such ranges unless the context clearly indicates otherwise. Thus, to illustrate, reference to a numerical range, such as 1-10 includes 1, 2, 3, 4, 5, 6, 7, 8, 9, 10, as well as 1.1, 1.2, 1.3, 1.4, 1.5, etc., and so forth. Reference to a range of 1-50 therefore includes 1, 2, 3, 4, 5, 6, 7, 8, 9, 10, 11, 12, 13, 14, 15, 16, 17, 18, 19, 20, etc., up to and including 50, as well as 1.1, 1.2, 1.3, 1.4, 1.5, etc., 2.1, 2.2, 2.3, 2.4, 2.5, etc., and so forth. Reference to a series of ranges includes ranges which combine the values of the boundaries of different ranges within the series. Thus, to illustrate reference to a series of ranges, for example, a range of 1-1,000 includes, for example, 1-10, 10-20, 20-30, 30-40, 40-50, 50-60, 60-75, 75-100, 100-150, 150-200, 200-250, 250-300, 300-400, 400-500, 500-750, 750-1,000, and includes ranges of 1-20, 10-50, 50-100, 100-500, and 500-1,000. The range 100 units to 2000 units therefore refers to and includes all values or ranges of values of the units, and fractions of the values of the units and integers within said range, including for example, but not limited to 100 units to 1000 units, 100 units to 500 units, 200 units to 1000 units, 300 units to 1500 units, 400 units to 2000 units, 500 units to 2000 units, 500 units to 1000 units, 250 units to 1750 units, 250 units to 1200 units, 750 units to 2000 units, 150 units to 1500 units, 100 units to 1250 units, and 800 units to 1200 units. Any two values within the range of about 100 units to about 2000 units therefore can be used to set the lower and upper boundaries of a range in accordance with the embodiments of the present disclosure.

The term "pharmaceutically acceptable" refers to compounds and compositions which are suitable for administration to humans and/or animals without undue adverse side effects such as toxicity, irritation and/or allergic response commensurate with a reasonable benefit/risk ratio.

By "biologically active" is meant the ability of an active agent to modify the physiological system of an organism without reference to how the active agent has its physiological effects.

As used herein, "pure," "substantially pure," or "isolated" means an object species is the predominant species present (i.e., on a molar basis it is more abundant than any other object species in the composition thereof), and particularly a substantially purified fraction is a composition wherein the object species comprises at least about 50 percent (on a molar basis) of all macromolecular species present. Generally, a substantially pure composition will comprise more than about 80% of all macromolecular species present in the composition, more particularly more than about 85%, more than about 90%, more than about 95%, or more than about 99%. The term "pure" or "substantially pure" also refers to preparations where the object species (e.g., the peptide compound) is at least 60% (w/w) pure, or at least 70% (w/w) pure, or at least 75% (w/w) pure, or at least 80% (w/w) pure, or at least 85% (w/w) pure, or at least 90% (w/w) pure, or at least 92% (w/w) pure, or at least 95% (w/w) pure, or at least 96% (w/w) pure, or at least 97% (w/w) pure, or at least 98% (w/w) pure, or at least 99% (w/w) pure, or 100% (w/w) pure. Where used herein the term "high specificity" refers to a specificity of at least 90%, or at least 91%, or at least 92%, or at least 93%, or at least 94%, or at least 95%, or at least 96%, or at least 97%, or at least 98%, or at least 99%. Where used herein the term "high sensitivity" refers to a sensitivity of at least 90%, or at least 91%, or at least 92%, or at least 93%, or at least 94%, or at least 95%, or at least 96%, or at least 97%, or at least 98%, or at least 99%.

The terms "subject" and "patient" are used interchangeably herein and will be understood to refer an organism to which the compositions of the present disclosure are applied and used, such as a vertebrate or more particularly to a warm blooded animal, such as a mammal or bird. Non-limiting examples of animals within the scope and meaning of this term include dogs, cats, rats, mice, guinea pigs, chinchillas, rabbits, horses, goats, cattle, sheep, llamas, zoo animals, Old and New World monkeys, non-human primates, and humans.

"Treatment" refers to therapeutic treatments, such as for bone defect healing. The term "treating" refers to administering the composition to a patient such therapeutic purposes, and may result in an amelioration of the condition or disease.

The terms "therapeutic composition" and "pharmaceutical composition" refer to an active agent composition, such as the BTE constructs described herein, that may be administered to a subject by any method known in the art or otherwise contemplated herein, wherein administration of the composition brings about a therapeutic effect as described elsewhere herein. In addition, certain compositions of the present disclosure may be designed to provide delayed, controlled, extended, and/or sustained release using formulation techniques which are well known in the art.

The term "effective amount" refers to an amount of an active agent which is sufficient to exhibit a detectable biochemical and/or therapeutic effect, for example without excessive adverse side effects (such as toxicity, irritation and allergic response) commensurate with a reasonable benefit/risk ratio when used in the manner of the present disclosure. The effective amount for a patient will depend upon the type of patient, the patient's size and health, the nature and severity of the condition to be treated, the method of administration, the duration of treatment, the nature of concurrent therapy (if any), the specific formulations employed, and the like. Thus, it is not possible to specify an exact effective amount in advance. However, the effective amount for a given situation can be determined by a person of ordinary skill in the art using routine experimentation based on the information provided herein.

The term "ameliorate" means a detectable or measurable improvement in a subject's condition or or symptom thereof. A detectable or measurable improvement includes a subjective or objective decrease, reduction, inhibition, suppression, limit or control in the occurrence, frequency, severity, progression, or duration of the condition, or an improvement in a symptom or an underlying cause or a consequence of the condition, or a reversal of the condition. A successful treatment outcome can lead to a "therapeutic effect," or "benefit" of ameliorating, decreasing, reducing, inhibiting, suppressing, limiting, controlling or preventing the occurrence, frequency, severity, progression, or duration of a condition, or consequences of the condition in a subject.

A decrease or reduction in worsening, such as stabilizing the condition, is also a successful treatment outcome. A therapeutic benefit therefore need not be complete ablation or reversal of the condition, or any one, most or all adverse symptoms, complications, consequences or underlying causes associated with the condition. Thus, a satisfactory endpoint may be achieved when there is an incremental improvement such as a partial decrease, reduction, inhibition, suppression, limit, control or prevention in the occurrence, frequency, severity, progression, or duration, or inhibition or reversal of the condition (e.g., stabilizing), over a short or long duration of time (e.g., seconds, minutes, hours).

Returning to discussion of particular embodiments of the present disclosure, within biomedical engineering, the field of tissue engineering primarily addresses shortcomings in tissue damage repair and organ transplants. By developing techniques for in vitro tissue culture and development, tissue engineering presents solutions to tissue damage-related problems which are unavailable to purely in vivo treatments. In many cases, treatment for tissue damage involves direct autologous transplant of a similar tissue from another region within the body. This approach repairs critically damaged tissue at the cost of tissue strength and integrity from the donor site. The tissue engineering approach instead extracts adult stem cells from the host nondestructively. These cells are then cultured in vitro with scaffolding, media, and flow stresses which mimic an in vivo environment, allowing the stem cells to proliferate and then differentiate into cell types which effect the desired tissue. Once properly developed, the tissue matrix is reinserted at the location requiring tissue repair, providing both material to provide support and cells optimized to mend the damaged tissue.

Bone tissue engineering utilizes mesenchymal stem cells (MSCs) derived from bone marrow extract to produce osteoblasts, a key component in bone development and maintenance. Osteoblastic tissue constructs developed in vitro will be used as grafts for delayed union or nonunion bone fractures. Currently, about 1 million delayed union or nonunion fractures occur in the U.S. each year. Standard treatment for these conditions involve an autologous bone graft, usually bone material removed from the hip. This method creates significant risk of morbidity and infection at the donor site as well as reducing the mechanical integrity of the hip bone. Development of a similar graft from MSCs would circumvent these complications.

The properties of the scaffold which supports the stem cells play a significant role in cell growth and differentiation and tissue development. As the supporting structure, the scaffold needs an appropriate degree of rigidity for the target tissue. Bone tissue in particular requires rigid scaffolding. Additionally, scaffolding requires porosity or maximal surface area for nutrient transfer and cell expansion. Scaffolds should also promote cell adhesion or they would not be viable surfaces for cell culture. When exposed to the tissue's native conditions, the scaffold should degrade at a rate similar to tissue development into a non-toxic product.

Scaffolds are a necessity for supporting cells in in vitro applications of tissue engineering. For bone tissue engineering, the scaffold must allow the cells to not only attach and proliferate, but must also allow for mechanical stimulation, encourage bone cell migration, act as a substrate for osteoid deposition, and deliver bioactive molecules. Another aspect that is desired is biodegradability. If a tissue engineered construct is put into the body, the scaffold must degrade over time leaving only organic material that will retain natural levels of mechanical strength. The common scaffold types used for bone growth are natural polymers (fibrin and collagen), synthetic polymers (polycarbonates, polyanhidrides, poly(ethylene oxide), polyfumarates, and polyphosphazene), metals and ceramics. Examples of biodegradable polymers which have been used include poly(lactic acid) (PLA), poly(L-lactic acid) (PLLA), poly(glycolic acid) (PGA), and poly(lactic-co-glycolic acid) (PLGA).

In at least certain embodiments, the scaffolds of the present disclosure may be composed of a low molecular weight (lowMW) polymer selected from the group consisting of polylactic acid (PLA), polyglycolic acid (PGA), poly caprolactone (PCL), poly (lactide-co-glycolide) (PLGA), poly (lactic acid/glycolic acid) (PLAGA), poly (lactide-co-caprolactone), poly (glycolide-co-caprolactone), poly (lactide-co-trimethylene carbonate), poly (glycolide-co-trimethylene carbonate), poly (lactide-co-glycolide-co-caprolactone), and poly (lactide-co-glycolide-co-trimethylene carbonate), and mixtures thereof.

In at least certain embodiments, the scaffolds of the present disclosure may be composed of a high molecular weight (highMW) polymer selected from the group consisting of polylactic acid (PLA), polyglycolic acid (PGA), poly caprolactone (PCL), poly (lactide-co-glycolide) (PLGA), poly (lactic acid/glycolic acid) (PLAGA), poly (lactide-co-caprolactone), poly (glycolide-co-caprolactone), poly (lactide-co-trimethylene carbonate), poly (glycolide-co-trimethylene carbonate), poly (lactide-co-glycolide-co-caprolactone), and poly (lactide-co-glycolide-co-trimethylene carbonate), and mixtures thereof.

In at least certain embodiments, the weight average MW of the lowMW polymer used herein for bulk preparation or surface modification of the scaffolds is less than 1000 Da (e.g., 500 Da to 1000 Da), or less than 1250 Da, or less than 1500 Da, or less than 2000 Da, or less than 2250 Da, or less than 2500 Da, or less than 2750 Da, or less than 3000 MW Da, or less than 4000 MW Da, or less than 5000 Da, and is at least partially water-soluble.

In at least certain embodiments, the weight average MW of the highMW polymer molecules used herein for bulk preparation or for scaffolds that are surface modified is at least 5000 Da, at least 10,000 Da, at least 20,000 Da, at least 25,000 Da, at least 50,000 Da, at least 75,000 Da, at least 100,000 Da, at least 125,000 Da, at least 150,000 Da, at least 175,000 Da, at least 200,000 Da, at least 250,000 Da, at least 300,000 Da, at least 400,000 Da, at least 500,000 Da, at least 600,000 Da, at least 700,000 Da, at least 800,000 Da, at least 900,000 Da, or at least 1,000,000 Da.

When bone cells are desired, osteogenic induction media (OIM) is used. The term "osteogenic differentiation media" (ODM) may be used interchangeably herein with osteogenic induction media. OIM differs from regular culture media (e.g., α-MEM) in that it contains dexamethasone, beta-glycerophosphate, and ascorbic acid. Dexamethasone is a glucocorticoid that has been found to facilitate bone differentiation and mineralization in cultures. Beta-glycerophosphate and ascorbic acid roles are to provide phosphate and increase collagen fibril production, respectively. The OIM may also include growth factors to aid in osteogenic differentiation. For example, non-limiting examples of such growth factors include bone morphogenetic proteins (BMP-2 to BMP-14), such as BMP-2 and BMP-7, are osteoinductive growth factors that are commonly used as growth factors to enhance mesenchymal stem cell differentiation into osteoblasts and may optionally be included in the OIM. BMP-2 is an important growth factor as it is involved in the TGF beta-signaling pathway, and aids in osteogenesis, cell growth, and differentiation. Osteogenic peptides derived from the BMPs may be used as well, for example as shown in U.S. Pat. No. 8,066,980. Non-limiting examples of OIMs (i.e., ODMs) that may be used herein include, but are not limited to, those shown in U.S. Pat. Nos. 9,334,481; 9,339, 520; 9,597,359; 9,808,558; and 9,814,803. Once the cells are ready to be used, they must be seeded onto the scaffolds. Although the procedure may vary, static and dynamic seeding are the two most commonly used seeding methods. Static seeding consists of injecting cells onto scaffolds that are sitting in a culture well plate. In dynamic seeding, the cells suspended in media are allowed to flow through the scaffold. In theory, this allows for a greater level of cell penetration.

Perfusion bioreactors have been shown to be the most effective systems for bone tissue engineering, and it has been found that they deliver a wide range of easily manipulated shear stresses to stimulate differentiation into bone cells. They usually comprise a pump, media reservoirs, scaffold chambers, and connecting tubes. There are two main types of perfusion bioreactors: scaffold perfusion, and perfusion column. Perfusion columns have space surrounding the scaffolds, through which the media can flow. By doing this, media is not required to flow throughout the scaffold and therefore the shear stresses are not as easily controlled, and nutrient delivery is lowered through the interior porosity of the scaffolds. Scaffold perfusion bioreactors give better control of shear stresses by flowing media directly through the scaffolds. This is accomplished by press-fitting the scaffold in a cassette that restricts fluid flow only through the pores of the scaffold. Assuming pore interconnectivity throughout the scaffold, fluid flow provides enhanced nutrient delivery to cells residing in all locations of the construct, and allow for better waste removal as well.

The main benefit for utilizing dynamic bioreactor culture is the mitigation of mass transport limitations. During extended culture, it is necessary to continually supply the cells with nutrients, such as oxygen and glucose, for them to continue to proliferate and differentiate. In static culture without media flow, nutrients are transported to the cells in the interior of the scaffold mainly by passive diffusion. Previous studies have shown that tissues above 600 µm suffer from large hypoxic areas. Therefore, only cells located near the periphery of the scaffold will have the nutrients required to proliferate. In order to culture constructs of clinically relevant size, it is necessary for bone tissue engineers to develop culture techniques that improve these undesirable nutrient gradients by adding convective mass transfer.

Perfusion bioreactors provide enhanced mass transport benefits. Due to the press fit cassettes, media is not only continuously supplied to the scaffold, but it also forced exclusively through the interior of the scaffold. By doing this, the nutrient gradient is mitigated, thus allowing cells to proliferate without experiencing severe hypoxic conditions. In addition to this, the unidirectional flow allows for continual waste removal from the scaffold. Examples of perfusions bioreactors which may be used in certain embodiments of the present disclosure include but are not limited to those shown in PCT application PCT/US2018/41972, published US patent applications 2011/0229970, 2012/0035742, 2016/0201037, 2016/0282338, 2016/0324642, and U.S. Pat. No. 8,367,059.

In the body, fluid flow induced shear forces give signals to mesenchymal stem cells to differentiate. As a force is applied to the bone, a pressure change occurs which leads to fluid flow inside the lacunae and canaliculi, leading to a signal transduction pathway resulting in these stem cells to differentiate into osteoblasts. In in vitro environments, previous research has shown shear stresses below 15 dynes/cm$^2$ to have a stimulatory effect promoting osteoblastic differentiation, matrix deposition and calcification, cell proliferation, and osteogenic gene expression in 3D constructs. Osteoblastic differentiation is more pronounced in scaffold perfusion systems. Due to media being forced through the interior of the scaffold, the average flow induced shear forces are more controllable and more evenly distributed throughout the scaffold.

Cell seeding is the first step in the development of in vitro bone tissue engineered constructs. Before a tissue can be grown, it is necessary to adhere cells to the surface of the scaffold, so that they may proliferate throughout the construct. In most cases, it is preferable to have a homogeneous seeding distribution so that the tissue can grow evenly across the entirety of the scaffold surface area. This is especially true in bone tissue engineering, where the cells must not only proliferate, but also deposit mineralized tissue. In terms of cellular adherence, this is measured in seeding efficiency, which is the number of cells adhered at the end of a seeding protocol in comparison to the number of cells that were initially placed on the construct.

In light of the aforementioned goals, static seeding is largely unsuitable. In static seeding, cells are suspended in media and either pipetted onto the surface of the scaffold or the scaffold is placed into the suspension. There are many techniques employed, such as vacuum evacuation or shaker plates, to induce cellular migration to the interior of the scaffold; however, the results suffer from inconsistencies and more often than usual demonstrate extended inhomogeneities that are clearly undesirable. Similar to the mass transport limitations that plague static cultures, cells to inhabit the periphery of the scaffold leading to nonhomogeneous tissue development.

In dynamic seeding, the cells are added to media, and fluid flow is utilized in the bioreactor system to help the cells navigate to the scaffold surface and potentially to the interior. The addition of flow produces higher seeding efficiency and a more homogenous cell distribution. Although each of the discussed dynamic bioreactor designs may be used to accomplish this, the perfusion bioreactor is once again more efficient at completing this task. Oscillatory seeding comprises adding the cells to the media and then using a flow perfusion system to alternate the flow direction making sure that the residence time is adequate to permit cells to fully travel through the scaffold before flow direction is changed. By doing this, cells are forced back and forth, through the interior of the scaffold many times over. Using this method, seeding efficiencies are increased even more so than with unidirectional flow.

In at least one example of the work shown below, rat MSCs were seeded on porous spunbonded PLLA scaffolds. The seeded scaffolds were cultured in flow perfusion bioreactors with baseline or osteoinductive media, and levels of key physio-metabolic markers (oxygen, glucose, osteoprotegerin, and osteocalcin) were monitored throughout culture. Comparison of these non-destructively obtained values and current standard destructive analyses demonstrated key trends useful for the concurrent real-time monitoring of construct cellularity and maturation. Principle among these was the elucidation of the ratio of the rates of oxygen uptake to glucose consumption as a powerful quality marker. This ratio, supported on a physiological basis, has been demonstrated herein to be a reliable marker in the determination of both construct maturation (defined as osteoblastic differentiation and accompanying mineralization) and construct cellularity. Supplementary monitoring of osteoprotegerin (OPG) and osteocalcin (OCN) are shown to provide further validation of such metrics.

EXAMPLES

Certain embodiments of the present disclosure will now be discussed in terms of several specific, non-limiting, examples. The examples described below will serve to illustrate the general practice of the present disclosure, it being understood that the particulars shown are merely exemplary for purposes of illustrative discussion of particular embodiments of the present disclosure only and are not intended to be limiting of the claims of the present disclosure.

Constructs comprising scaffolds seeded with mesenchymal stem cells (MSCs) were cultured in flow perfusion bioreactors in either or osteoinductive ("osteo" or OIM) or basal (non-osteoinductive) media ("MEM") and monitored throughout culture periods of up to 14 days. Constructs were then sacrificed at various time points (e.g., Day 1, 3, 5, 7, 9, 11, and 14) and analyzed for key quality markers of cellularity, alkaline phosphatase activity, and calcium deposition, among others. Retrospective analysis was then performed to correlate the mid-culture monitoring data with post-sacrificial analyses and develop proposed metrics for quality control and monitoring purposes. The resulting data revealed a promising metric for the monitoring of BTE constructs throughout differentiation and proliferation, enabling real-time quality control and determination of optimal implant timing.

Methods

Cell Extraction and Isolation

Rats were housed and sacrificed under the approval of the IACUC (institutional protocol number: R15-008). Rat mesenchymal stem cells (rMSCs) were isolated from marrow extracted from the femurs and tibias of adult male Wistar rats approximately 6 weeks of age (175-199 g in mass; Envigo) utilizing established methods. Extracted marrow was pooled, homogenized, and divided into T75 culture flasks. Three days post-extraction flasks were rinsed thoroughly with Dulbecco's phosphate buffered saline (PBS; gibco) to remove any non-adherent cells; the remaining adherent cells constituted passage zero rMSCs.

Cell Culture and Expansion

Cells were cultured in α-Minimum Essential Media (MEM; Gibco) supplemented with 10% fetal bovine serum (FBS; Atlanta Biologics) and 1% antibiotic-antimycotic (Gemini BioProducts) within T75 cell-culture flasks at 37° C., 95% relative humidity, and 5% $CO_2$. Media was replaced every other day until cells reached a maximum confluency of 80%, at which time they were passaged. Cells were harvested after passage 2 for bioreactor seeding.

Bioreactor System

The bioreactor system used herein is of the flow perfusion type, based on the design of Bancroft et al, 2003, a design comprising a main body with 6 individual reservoirs into which cassettes with immobilized scaffolds were secured, allowing for direct perfusion of media through each scaffold at a rate of 150 μL/min. Oxygen-permeable tubing used throughout the system allowed for full re-oxygenation of media between passes through the constructs. A global media reservoir system allowed for easy media replacement and sampling. Any suitable flow perfusion bioreactor in which equivalent volumes of media are simultaneously added and removed from the bioreactor while the scaffold is held in the bioreactor, and which enables sampling of the removed media, can be used.

Scaffold Production

Nonwoven fiber mesh scaffolds were prepared from poly (L-lactic acid) (PLLA; grade 6251D; 1.4% D enantiomer; 108,500 MW; 1.87 PDI; NatureWorks LLC) via spunbonding. Scaffolds 5 mm thick and 8 mm in diameter were cut from nonwoven sheets. Resulting scaffold properties were: average fiber diameter of 25 μm, average pore size of 250 μm, and overall porosity of 88%.

Scaffold Pre-Seeding Treatments

Sterilized scaffolds were subjected to two consecutive pre-seeding treatments: pre-wetting and serum exposure. Pre-wetting was performed by submerging scaffolds in 95% ethanol under vacuum before transferring them to PBS to ensure liquid penetration of the entire porosity of said scaffolds thereby facilitating seeding. Serum exposure was performed for one hour prior to cell seeding to facilitate cell attachment.

Bioreactor Seeding and Culture

Scaffolds were seeded within bioreactors utilizing an oscillatory seeding regimen adapted from Alvarez-Barreto et al., 2007. Two million cells suspended within 150 μL of media were pipetted directly on top of each scaffold and subsequently subjected to oscillatory flow perfusion at a rate of 150 μL/min with a period of oscillation of 1 minute (i.e., 1 min forward flow, 1 min reverse flow, etc.) for a total of 1 hour. This dynamic regimen was followed by a rest period (i.e., no flow) of 2 hours. The entire media volume was then replaced with fresh media prior to reintroducing flow (to remove any unattached cells).

At this point, bioreactors were subjected to one of two different media formulations (baseline and osteogenic inductive) for the remainder of the culture period. The baseline media was MEM (as described above). The osteogenic induction media (OIM), also referred to herein as osteoinduction media (and abbreviated as "Osteo"), was prepared from baseline media (α-MEM) with the addition of 50 mg/L of L-ascorbic acid (Sigma), 10 mM β-glycerophosphate (Sigma), and 10 nM dexamethasone (Sigma). The media within each bioreactor was replaced every other day with fresh media such that a total volume of 16.67 mL of media per construct was maintained. Any suitable OIM can be used herein and it is not intended to limit the embodiments of the present disclosure to this specific OIM formulation.

Mid-Culture Species Sampling and Rate Calculations

Oxygen Uptake

Oxygen measurements were taken at the inlet and outlet of each construct every other day with the use of the NeoFox Kit with RedEye® oxygen sensing patches (Ocean Optics). Dissolved oxygen measurements were obtained with the use of in-house made oxygen sensing modules (OxyMods) comprised of RedEye® patches affixed to the interior of square glass tubing segments with glass reducers attached at either end. Non-oxygen permeable tubing was used to connect these OxyMods in line with the flow through each construct (such that re-oxygenation of media between sampling points was not a concern). The NeoFox software along with the RedEye® patch pre-calibration and an in-house calibration offset (to account for signal loss through the glass tubing) resulted in oxygen concentration data (provided in PPM) based on the Stern-Volmer equation with a temperature correction (calculated within the NeoFox program). All measurements were recorded after a levelling-off in the readout value.

The resulting steady-state mass balance on oxygen within the direct-perfusion system (through each individual construct), assuming zero-order kinetics for the uptake of oxygen by the cells was derived to be:

$$[C_{O_2,in} - C_{O_2,out}] \times v = OUR_{construct} \quad \text{(Eqn. 1a)}$$

$$= N_{cells} \times q_{O_2} \quad \text{(Eqn. 1b)}$$

where $C_{O_2}$=concentration of $O_2$ (subscripts "in" and "out" correspond to inlet and outlet of construct, respectively); mol vol$^{-1}$ v=volumetric flow rate of media through construct; vol time$^{-1}$ $OUR_{construct}$=construct-specific oxygen uptake rate; mol construct$^{-1}$ time$^{-1}$ $N_{cells}$=number of cells within each construct $q_{O_2}$=cell-specific oxygen uptake rate; mol cell$^{-1}$ time$^{-1}$ Glucose Consumption Glucose measurements were taken on media samples obtained from the global media reservoir every other day with the use of the GlucCell™ Glucose Monitoring System (CESCO BioProducts) per the instructions. Briefly, a 10 µL media sample was pipetted onto a fresh GlucCell™ test strip for glucose assay (results given in mM).

The resulting steady-state mass balance on glucose within the global bioreactor system, assuming glucose is well-mixed throughout the system and zero-order kinetics for the consumption of glucose by the cells was derived to be:

$$\frac{[C_{glc,0} - C_{glc,\Delta t}]}{\Delta t} = \frac{GCR_{global}}{V_{media,tot}} \quad \text{(Eqn. 2a)}$$

$$= \frac{N_{constructs} * GCR_{construct}}{V_{media,tot}} \quad \text{(Eqn. 2b)}$$

$$= \frac{N_{cells} * N_{constructs} * q_{glc}}{V_{media,tot}} \quad \text{(Eqn. 2c)}$$

where $C_{glc}$=concentration of glucose (subscripts "0" and "$\Delta t$" correspond to time of media change and time of media sample, respectively); mol vol$^{-1}$ $N_{constructs}$=number of active constructs in bioreactor system $q_{glc}$=cell-specific glucose consumption rate; mol cell$^{-1}$ time$^{-1}$ $V_{media,tot}$=total volume of media in bioreactor over time $\Delta t$, vol $GCR_{global}$=global glucose consumption rate; mol time$^{-1}$ $GCR_{construct}$=construct glucose consumption rate mol construct$^{-1}$ time$^{-1}$ Osteoprotegerin and Osteocalcin Production Osteoprotegerin (OPG) and osteocalcin (OCN) measurements were taken on media with the use of enzyme-linked immuno-sorbent assays (ELISA; Lifespan Biosciences) per assay instructions (with detection ranges of 15.6-1000 and 62-4000 pg/mL, respectively). Briefly, samples or standards were pipetted into each well and incubated for 2 hours, wells were then washed, incubated with detection reagent A for 1 hour, washed, incubated with detection reagent B for 1 hour, washed, incubated with 3,3',5,5'-Tetramethylbenzidine (TMB) substrate for 30 min, and then quenched with stop solution and immediately read on a Synergy HT microplate reader (Bio-Tek) at 450 nm (all incubations were carried out in obscurity at 37° C.). All samples and standards were run in duplicate per kit recommendation.

Similarly to that of glucose, and with the same assumptions (in addition to the assumption of negligible degradation of OPG by endogenous proteases, which was tested and found to be a viable assumption), the resulting steady state mass balance on OPG was derived to be:

$$\frac{[C_{OPG,\Delta t} - C_{OPG,0}]}{\Delta t} = \frac{OPGPR_{global}}{V_{media,tot}} \quad \text{(Eqn. 3a)}$$

$$= \frac{N_{constructs} * OPGPR_{construct}}{V_{media,tot}} \quad \text{(Eqn. 3b)}$$

$$= \frac{N_{cells} * N_{constructs} * p_{OPG}}{V_{media,tot}} \quad \text{(Eqn. 3c)}$$

where $C_{OPG}$=concentration of OPG (subscripts "0" and "$\Delta t$" correspond to time of media change and time of media sample, respectively); mol vol$^{-1}$ $p_{OPG}$=cell-specific OPG production rate; mol cell$^{-1}$ time$^{-1}$ $OPGPR_{global}$=global OPG production rate; mol time$^{-1}$ $OPGPR_{construct}$=construct OPG production rate; mol construct$^{-1}$ time$^{-1}$ An identical set of equations could be developed for OCN as well.

Post-Culture Quality Analyses

The construct quality markers of cellularity, alkaline phosphatase activity, and calcium deposition were quantified from constructs sacrificed on days 1, 3, 5, 7, 9, 11, and 14 which were rinsed in PBS, torn apart into 1 mL of nanopure water, and subjected to 3 freeze-thaw cycles followed by brief sonication. All samples were obtained from the resulting liquid comprised of cell lysate solubilized in water.

Cellularity Quantification

Construct cellularity was determined via quantification of dsDNA with the use of a Quant-iT™ PicoGreen® dsDNA assay kit (Invitrogen). Briefly, 43 µL of sample or standard was pipetted into each well of an opaque 96-well plate to which 257 µL of reaction mixture (10 mM Tris-HCl, 1 mM EDTA, 1.3 µL PicoGreen® reagent, pH 7.5) was added. The plate was incubated for 5 min in obscurity and subsequently read on a Synergy HT microplate reader (Bio-Tek) at excitation/emission settings of 490/520 nm. Resulting fluorescent intensity values were used to quantify the amount of dsDNA in each sample. Said dsDNA values were then divided by per-cell dsDNA values determined experimentally (data not presented herein). The cellular dsDNA content was determined to be a constant 4.5 pg/cell for the baseline media group while that for the group cultured within osteo-inductive media was found to vary with time over the course of the culture period in accordance with Eqn 4.

$$\frac{m_{dsDNA}}{cell}(pg) = 4.5 - 0.0102t^2 \quad \text{(Eqn. 4)}$$

where t=culture time (in days).

Alkaline Phosphatase (ALP) Activity Quantification

Construct cellular ALP activity was determined using a fluorometric assay based on the enzymatic conversion of p-nitrophenol phosphate (pNPP) to p-nitrophenol (pNP). Briefly, 80 µL of each sample and standard were added to 20 µL of glycine buffer (0.1 M glycine, 1 mM MgCl2, 1 mM ZnCl2, pH 10.4) and 100 µL of substrate solution (1 mg/mL pNPP in glycine buffer) in a clear 96-well plate and allowed to incubate at 37° C. for 30 min before being quenched with the addition of 50 µL of 3.0 M NaOH and subsequently read on a Synergy HT microplate reader (Bio-Tek) at an absorbance wavelength of 410 nm.

Calcium Deposition Quantification

Construct calcium deposition was determined using a colorimetric calcium assay (Sigma) per assay instructions. Prior to assaying, remaining cell lysate solutions were diluted 1:1 in 1M acetic acid and incubated overnight to solubilize deposited calcium. 10 µL of the resulting solution (or sample) was added to 200 µL of buffered reagent solution (250 mM 2-amino-2-methyl-1,3 propanediol, 0.012% 8-hydroxyquinoline, and o-cresolphtalein Complexone®) in a clear 96-well plate which was subsequently read on a Synergy HT microplate reader (Bio-Tek) at an absorbance wavelength of 575 nm.

Statistical Analysis

Unless otherwise specified, all samples and standards were run in triplicate. Results are reported as mean±SEM with N=4 for the osteoinduction (Osteo) group; N=3 for the baseline (MEM) group (unless otherwise stated). Significance was calculated via two-way ANOVA with Tukey's HSD post-hoc analysis (* signifies p<0.05). Errors for derived values were calculated via the propagation of error method.

Determination of the Threshold

In one non-limiting embodiment, the OUR/GCR rate threshold (predetermined threshold) for determination of maturation of a BTE construct is about 2.0 (e.g., ±0.1, or ±0.2). It will be understood that the threshold can change depending on different culturing factors, such as number of cells ($N_{cells}$) or density of cells on the scaffold. The threshold can be predetermined on a case-by-case basis. For example, in the experimental methods shown herein (using a group incubated with baseline media and a group incubated with osteoinduction media), the OUR/GCR rate value for the two groups is calculated, and a statistically significant jump (divergence), (such as occurs at about 2.0 in FIG. 3) in the ratio that persists for at least 2 to 4 days provides a threshold for that type of bone cell construct. An experiment such as that used for FIG. 4 to determine calcium deposition can be used to confirm that newly calculated threshold provides a sufficiently mature bone construct. The calcium deposition in the bone construct is examined after removal from the perfusion bioreactor when the threshold is reached. If the bone construct has attained sufficient maturity (i.e., adequate calcium deposition), the effectiveness of the calculated OUR/GCR threshold is confirmed for future bone construct production.

Results

Construct Quality

Cellularity

Construct cellularity was seen to decline to a steady value by Day 5 for both groups, with significantly higher cellularity observed for the Osteo group. These values were observed to be 320,000±30,000 cells per construct for the Osteo group and 40,000±10,000 cells per construct for the MEM group. Previous studies in the lab have demonstrated near-homogenous cellular distribution throughout the constructs over time utilizing the same methods as employed herein.

Alkaline Phosphatase (ALP) Activity

Figure 1:
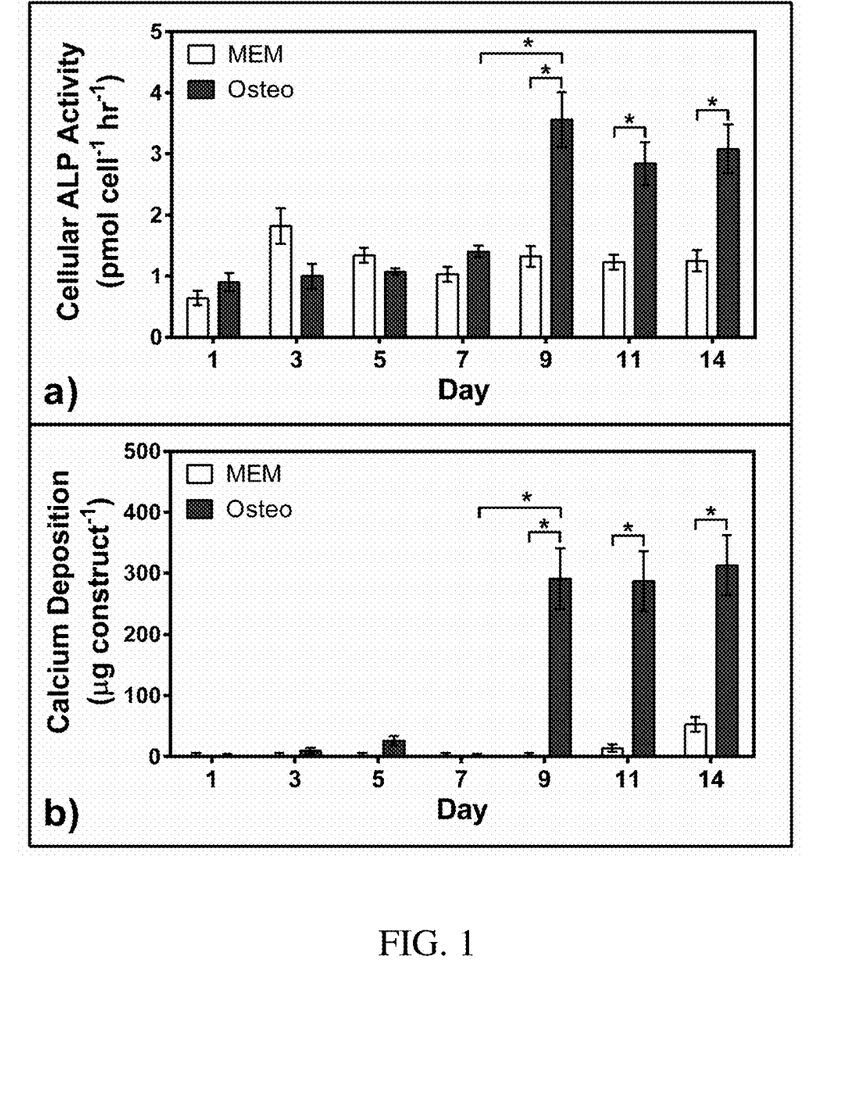
FIG. 1 shows quality markers of bone-tissue engineered constructs. (a) A baseline level of ALP is seen to be expressed by immature MSCs as evinced by steady expression through Day 7. The activity level of alkaline phosphatase per cell is seen to increase markedly between Days 7 and 9 for the group treated with osteogenic inductive (osteoinductive) media ("Osteo" group) while remaining at the baseline level in the group treated with Minimum Essential Media-α ("MEM" group). (b) A low level of calcium is initially present within each scaffold, which can be attributed to intracellular calcium. A significant increase in calcium deposited within the construct is observed between Day 7 and Day 9.

Alkaline phosphatase was observed to maintain constitutive activity (per-cell) for the entire culture duration for the MEM group at levels of approximately 1.2 pmol $hr^{-1}$ $cell^{-1}$ while the same values were observed for the Osteo group through Day 7. After Day 7, however, ALP activity was seen to dramatically increase to a level of approximately 3.0 pmol $hr^{-1}$ $cell^{-1}$ for the Osteo group, a value which was maintained for the remainder of the culture period (FIG. 1a).

Calcium Deposition

Total calcium present within sacrificed constructs was seen to remain very low through Day 7 for both groups. From Day 9 onward, minor (though not significant) increases in calcium content were observed for the MEM group while dramatic increases to levels near 300 ug/construct were observed for the Osteo group (FIG. 1b).

Mid-Culture Monitored Species Rates

Rate values obtained mid-culture were calculated on a per-construct basis. These per-construct values were subsequently normalized by construct cellularities (obtained subsequently via destructive means) resulting in cell-specific rates as a means of comparison between the treatment groups exhibiting different cellularities.

Cell-Specific Oxygen Uptake Rate, $q_{O2}$

Figure 2:
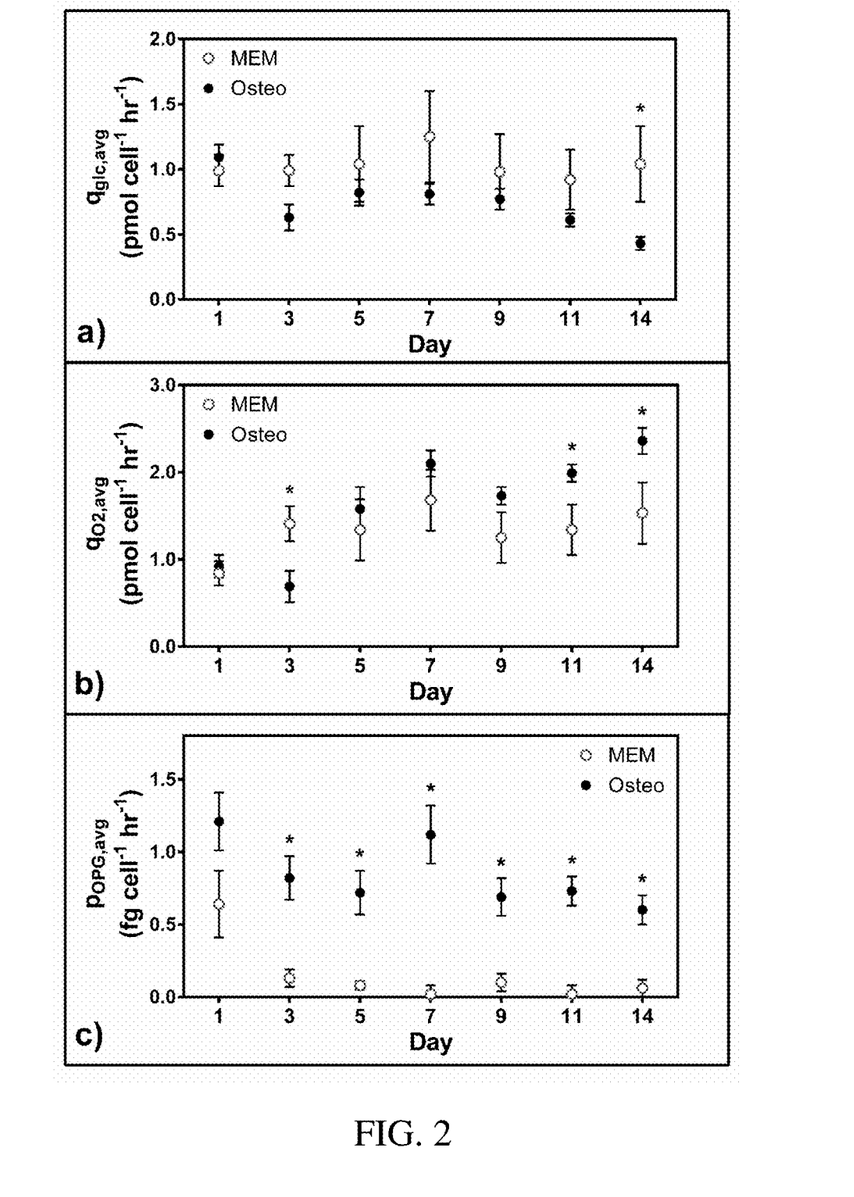
FIG. 2 shows mid-culture cell-specific physio-metabolic rates. Both the MEM and Osteo groups are seen to start at the same initial values for all rates as evinced by the data on Day 1. (a) $q_{O2,avg}$ is seen to remain steady for the MEM group while that for the Osteo group is seen to trend upwards. (b) $q_{glc,avg}$ is seen to remain steady for the MEM group while that for the Osteo group is seen to trend downwards. (c) the Osteo group is seen to maintain a steady $q_{OPG}$, whereas that for the MEM group is seen to fall off by Day 3, remaining low for the remainder of the culture period.

The average cell-specific oxygen uptake rate was observed to be approximately 1.0 pmol $O_2$ $hr^{-1}$ $cell^{-1}$ for both groups at the start of the culture period. This value was seen to increase for both groups, quickly leveling off to approximately 1.4 pmol $O_2$ $hr^{-1}$ $cell^{-1}$ for the MEM group while gradually rising over the course of the culture period for the Osteo group to a maximal value (observed at Day 14) of approximately 2.4 pmol $O_2$ $hr^{-1}$ $cell^{-1}$ (FIG. 2a).

Cell-Specific Glucose Consumption Rate, $q_{OPG}$

The average cell-specific glucose consumption rate was observed to be approximately 1.0 pmol glucose $hr^{-1}$ $cell^{-1}$ for both groups at the start of the culture period. This value was seen to remain constant over the course of the two-week culture period for the MEM group, while gradually declining to a minimal value (observed at Day 14) of approximately 0.4 pmol glucose $hr^{-1}$ $cell^{-1}$ for the Osteo group (FIG. 2b).

Cell-Specific Osteoprotegerin (OPG) Production Rate, $q_{OPG}$

The average cell-specific OPG production rate was observed on Day 1 to be approximately 1.0 fg OPG $hr^{-1}$ $cell^{-1}$ for both. Production of OPG was seen to remain at a constitutive level of ~0.7 fg OPG $hr^{-1}$ $cell^{-1}$ for the Osteo group while a steep decline to constitutive levels of about 0.1 fg OPG $hr^{-1}$ $cell^{-1}$ was seen for the MEM group (FIG. 2c).

Osteocalcin Production Rate

Although only detected at levels below the quantifiable detection limit of the assay, osteocalcin was detected at levels above the background in media samples obtained on Day 11 and Day 14 from the Osteo group. No osteocalcin was detected for the Osteo group at any earlier time points or at any time points for the MEM group.

Metabolic Ratio Analysis: $q_{O2}/q_{glc}$ (OUR/GCR)

With the assumptions made in the derivations of Eqn. 1 and Eqn. 2 (namely that of zero-order kinetics), it is easily seen that the ratio of the cell-specific rates, $q_{O2}$ and $q_{glc}$, is equal to that of their construct-specific counterparts, $OUR_{construct}$ and $GCR_{construct}$. As such, the term OUR/GCR is used henceforth to represent both ratios, a distinction discussed below.

OUR/GCR Over Time

Figure 3:
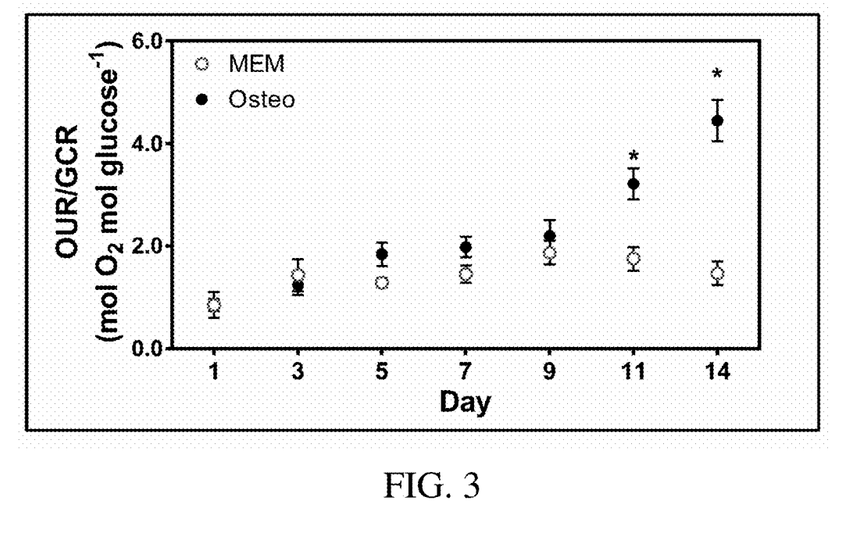
FIG. 3 shows ratios of oxygen uptake rate/glucose consumption rate (OUR/GCR) throughout the culture period. The ratio of construct-specific OUR/GCR values for the MEM group are seen to remain constant whereas those for the Osteo group trend upward with time. The ratios diverge at about 2.0 mol $O_2$/mol glucose.

The ratio of the rates of oxygen uptake and glucose consumption was seen to remain constant over the first week of culture for both groups, at an average value of approximately 1.2 mol $O_2$/mol glucose. During the second week of culture, however, a statistically significant divergence was observed wherein the MEM group maintained this ratio while that for the Osteo group was seen to increase to a maximal value (at Day 14) of greater than 4 mol $O_2$/mol glucose (FIG. 3).

OUR/GCR Versus ALP Activity and Calcium Deposition

Figure 4:
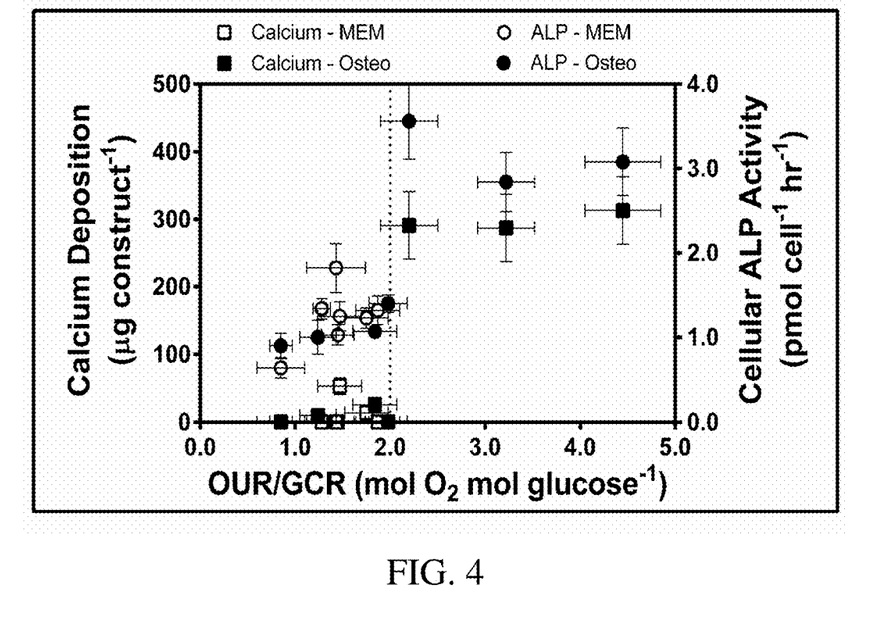

Observing the correlation in time between the divergence in the ratio of OUR/GCR between the groups (FIG. 3) and the marked increases in both ALP activity and calcium deposition (FIG. 1a and FIG. 1b, respectively), a plot comparing these values was constructed (FIG. 4). The calcium deposition at each time point for each group was plotted against the corresponding OUR/GCR ratio, resulting in 14 individual points (7 data points from the Osteo group and 7 points from the MEM group). The same was done for ALP activity data. A noticeable trend is apparent wherein all data points showing low calcium deposition and ALP activity levels had OUR/GCR ratios below 2.0, whereas all data points above 2.0 showed high calcium deposition and ALP activity levels (corresponding to the Osteo group at Days 9, 11, and 14).

OUR/GCR Ratio as a Metric for the Determination of Construct Cellularity

Figure 5:
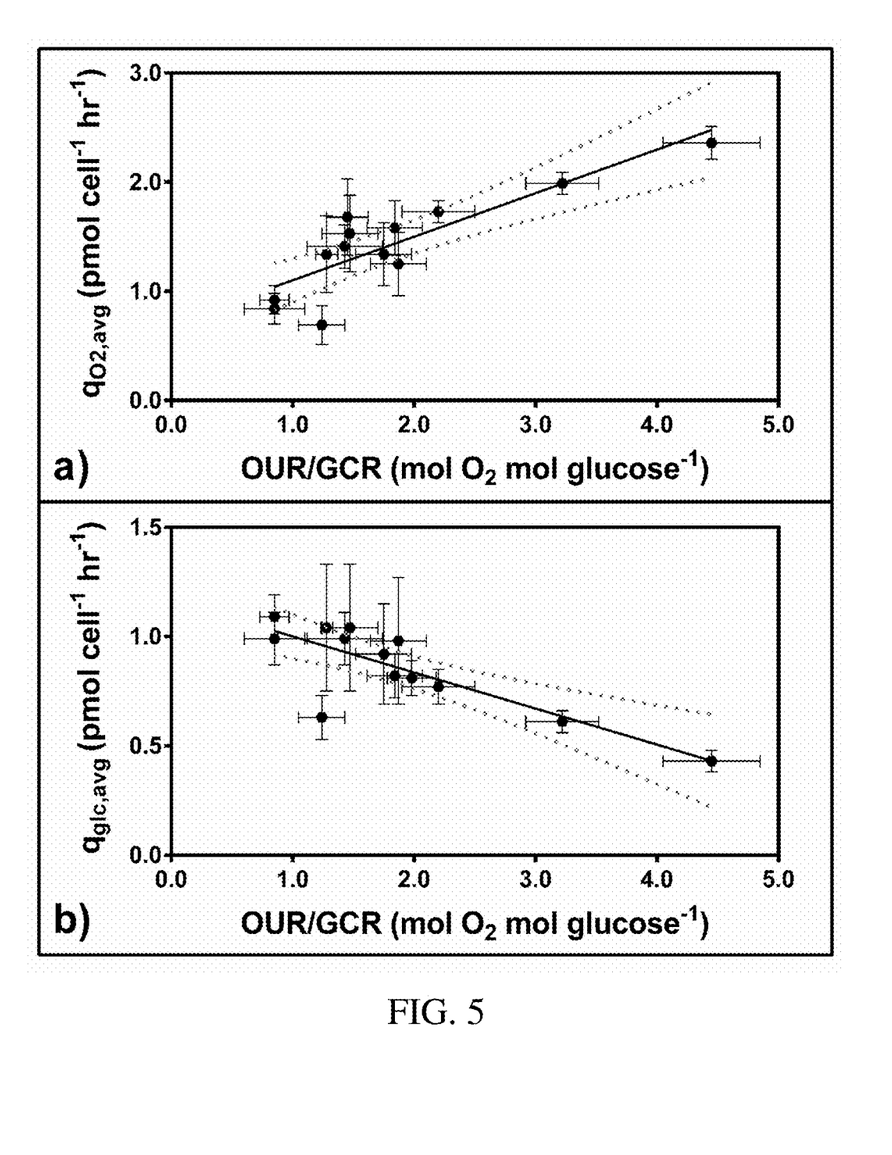
FIG. 5 shows OUR/GCR ratios versus cell-specific metabolic rates. (a) The cell-specific oxygen uptake rate as a function of OUR/GCR results in a positive correlation, with the linear regression (bold black line) resulting in Equation 5. (b) The cell-specific glucose consumption rate as a function of OUR/GCR results in a negative correlation, with the linear regression (bold black line) resulting in Equation 6. Dotted lines are 95% confidence intervals; one outlier was removed from each regression.

Using OUR/GCR to Determine Cell-Specific Metabolic Rates, $q_{O2}$ and $q_{glc}$ Observing the correlation in time between the aforementioned divergence in the OUR/GCR ratio and divergences in the cell-specific metabolic rates of oxygen and glucose (between the MEM and Osteo groups), plots comparing these data were constructed. A positive linear correlation exists between $q_{O2}$ and OUR/GCR (FIG. 5a), and a negative linear correlation exists between $q_{glc}$ and OUR/GCR (FIG. 5b). The resulting linear regressions of both plots are provided as Eqn. 5 and 6, respectively.

$$q_{O_2}\left(\frac{pmol}{hr\ cell}\right) = 0.70 + 0.40\left(\frac{OUR}{GCR}\right) \quad r^2 = 0.74 \quad \text{(Eqn. 5)}$$

$$q_{glc}\left(\frac{pmol}{hr\ cell}\right) = 1.17 - 0.16\left(\frac{OUR}{GCR}\right) \quad r^2 = 0.67 \quad \text{(Eqn. 6)}$$

Using OUR/GCR-Determined Cell-Specific Rates to Predict Cellularity

Utilizing the correlations developed above for the determination of the cell-specific rates of oxygen uptake and glucose consumption (Eq. 5 and Eqn. 6, respectively), along with their respective construct-specific counterparts (OUR and GCR, respectively), an estimation of the cellularity of each construct can be made by dividing the latter rates by the former ones (as can be derived from combination of Eqns. 1a and 1b for oxygen data or Eqns. 2b and 2c for glucose data, resulting in Eqn. 7 and Eqn. 8, respectively).

$$N_{cells} = \frac{OUR\left(\frac{\mu mol}{hr}\right)}{\left(0.70 + 0.40\left(\frac{OUR}{GCR}\right)\right)} \times 10^6 \quad \text{(Eqn. 7)}$$

$$N_{cells} = \frac{GCR\left(\frac{\mu mol}{hr}\right)}{\left(1.17 - 0.16\left(\frac{OUR}{GCR}\right)\right)} \times 10^6 \quad \text{(Eqn. 8)}$$

Figure 6:
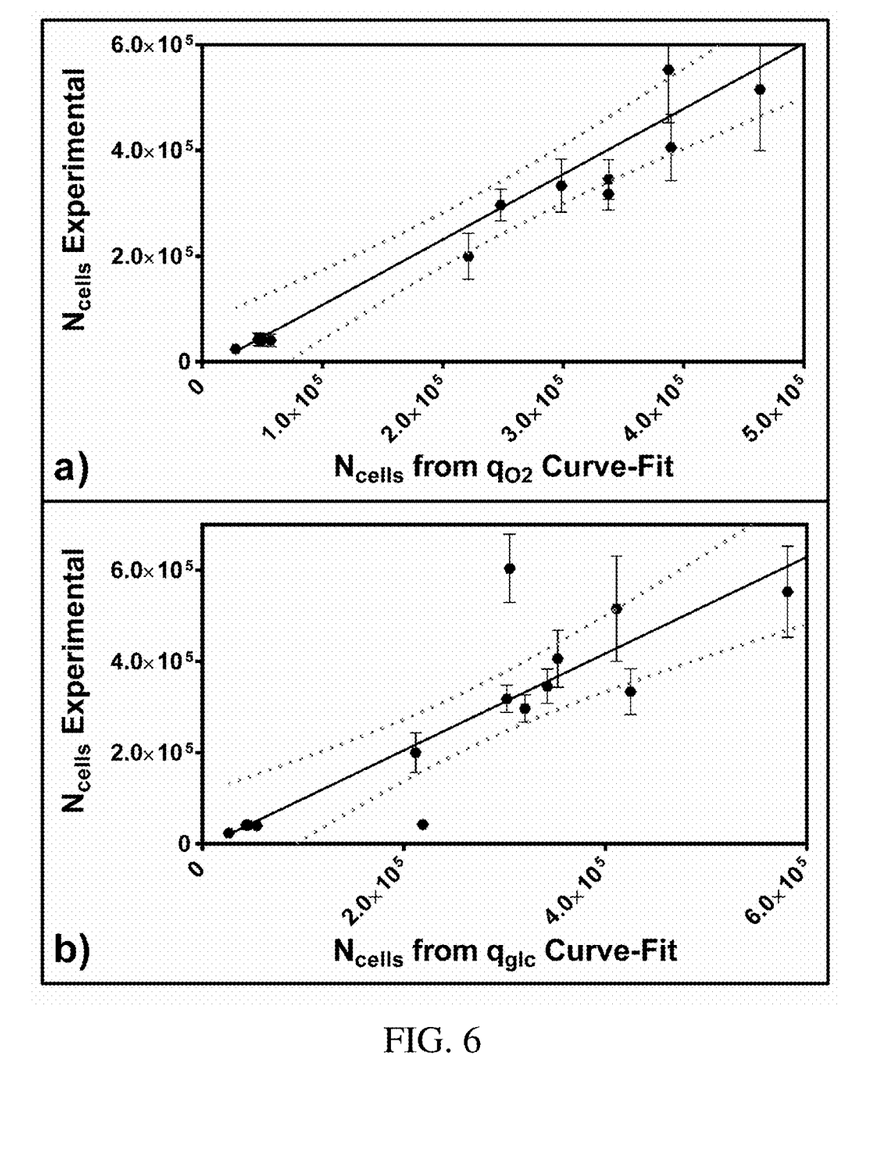
FIG. 6 shows experimental cellularity versus metabolic rate curve-fits for cellularity ($N_{cells}$=number of cells). (a) Construct cellularity via Equation 7 (a) or Equation 8 (b) vs. experimentally-determined cellularity. Linear regression of both plots result in fits, exhibiting slopes of 1.24 and 1.06, respectively; y-intercepts of −15,000 and −7,000, respectively; and $r^2$ values of 0.84 and 0.80, respectively. Dotted lines are 95% confidence intervals, revealing confidence of approximately ±20% of the experimentally-determined cellularity.

Comparisons of the cellularity predicted from the above equations alongside experimentally determined cellularity values demonstrate the strong predictive capabilities of both, as evident from linear regressions of each plot (FIG. 6). The lines of best fit produced for each plot exhibit slopes near 1.0, small aberrations from an ideal y-intercept of 0, and $r^2$ values near 0.80. Furthermore, the 95% confidence bands demonstrate a predictive capability of within approximately ±20% of the experimentally-determined cellularity from application of Eqn. 7 or Eqn. 8.

Discussion

Construct Quality

Utilizing the traditional destructively-obtained markers of bone tissue engineered construct quality (cellularity, ALP activity, and calcium deposition), it is evident from FIG. 1 that the Osteo treatment group (cultured within osteoinductive media) begins to mature into a bone-like construct within 9 days in culture (exhibiting increased ALP activity and calcium deposition along with maintenance of cellularity). Furthermore, the same figure demonstrates that the MEM group (cultured in basal media) does not show signs of osteo-maturation based on maintenance of steady ALP activity at basal levels and no significant increase in deposited calcium. Lower values of cellularity observed for the MEM group as compared with the Osteo group is potentially the result of decreased attachment potential of non-differentiating MSCs to an osteoconductive scaffold as compared with their osteo-differentiating counterparts.

Physio-Metabolic Rate Trends Throughout the Two-Week Culture Period

It is prudent to note that due to the macro-scale sampling methods employed herein (wherein construct-specific rates were measured directly, not cell-specific rates), all cell-specific rates discussed are more aptly referred to as average cell-specific rates. This distinction acknowledges the potential for non-zero-order kinetics (with respect to the species of interest) for each metabolic rate (i.e. the cell-specific rate of oxygen uptake may indeed be a function of the local concentration of oxygen). Based on the nature of the flow perfusion profile, gradients in the concentration of each species are inevitable, which could lead to variations in cell-specific metabolic rates. Furthermore, differences in differentiation status among cells within a construct could result in such variations as well. These effects were mitigated within the experiments detailed herein by the small concentration gradients (in space or time) resulting from the low cellularities employed.

The increase in oxygen uptake rate coupled with a decrease in glucose consumption rate suggests a shift in metabolic profile from a glycolytically-dominated metabolism to one benefiting from increased utilization of oxidative phosphorylation (FIG. 2). Indeed, this is a trend supported in the literature for the differentiation of MSCs into osteoblasts. Much higher rates of oxygen uptake and glucose consumption are reported herein as compared with the literature (Table 1). A possible explanation of this discrepancy is the nature of the quantification of these values present in the literature wherein large quantities of cells were cultured in stagnant 2D flasks. Such a system is prone to large concentration gradients, suffering from the complications discussed above.

TABLE 1

Summary of Calculated Cell-Specific Physio-Metabolic Rates

|  |  | Calculated Values (Day 14) | Literature Values | Reference |
|---|---|---|---|---|
| $q_{O_2}$ (fmol/hr/cell) | MSC | 1400 ± 600 | 100 ± 20 | Pattappa, et al., 2011 |
|  |  |  | 40 ± 10 | Komarova, et al. 2000 |
|  | Osteoblast | 2400 ± 300 | 200 ± 30 | Komarova, et al. 2000 |
| $q_{glc}$ (fmol/hr/cell) | MSC | 1000 ± 400 | 540 ± 80 | dos Santos, et al., 2010 |
|  |  |  | 250 ± 110 | Schop, et al., 2009 |
|  | Osteoblast | 400 ± 100 | — | — |
| $p_{OPG}$ (fg/hr/cell) | MSC | 0.1 ± 0.1 | — | — |
|  | Osteoblast | 0.7 ± 0.2 | — | — |

Cell-specific rates calculated herein compared with the literature (mean ± SD). Calculated values for MSC and osteoblast refer to Day 14 values for MEM and Osteo groups, respectively.

OPG, a regulatory signaling molecule, is stated in the literature to be expressed constitutively by immature MSCs with increased production in pre-osteoblasts and osteoblasts (though specific values for these rates are not readily available). Indeed, higher sustained rates of OPG production were observed for the Osteo group as compared with the MEM group. Higher initial values of OPG production (at Day 1) in both groups are thought to be an artifact of cellular acclimation to a new environment. Resulting values of cell-specific OPG production rates are presented in Table 1. It is notable that, as a regulatory signaling molecule, production rates of OPG are highly likely to be dependent on local concentrations (in addition to other environmental cues). As such, the rates presented herein may have been influenced by the intermittent replacement of media (resulting in loss of all previously-circulating OPG).

OCN, a bone-specific protein secreted by mature osteoblasts (and not MSCs or pre-osteoblasts), was found to be present within media samples only for the Osteo group at late time points (Day 11 and Day 14). Though detected at values near the lower quantifiable limit of the assay, it was consistently found to be present at levels above all background measurements in these two late time points. This late onset of osteocalcin production is observed to follow the significant increases in calcium deposition and ALP activity, demonstrating its potential as a non-destructive marker of late-term maturation of bone tissue engineered constructs from media assay.

Use of OUR/GCR for Monitoring BTE Constructs

As noted, the ratio of the microscopic (i.e. cell-specific) rates of oxygen uptake to glucose consumption matches the ratio of the macroscopic (i.e. construct-specific) rates; in other words $q_{O_2,avg}/q_{glc,avg}$=OUR/GCR. Though this equality may seem trivial, the functional impact is profound. This comes down to the fact that calculation of the former (microscopic rates) requires precise knowledge of the number of cells within a construct (a difficult task to achieve non-destructively in a 3D construct). Calculation of the later (macroscopic rates); however, is achieved much more easily, simply requiring measurement of a change in concentration (over space or time). Indeed, it is the power afforded by the utilization of a ratio of macroscopic rates (i.e., OUR/GCR) which circumvents the necessity of knowing the cellularity.

The correlation in time between the divergence (of the Osteo group from the MEM baseline) of the OUR/GCR ratio and the divergences of ALP activity and calcium deposition first suggested the potential of said ratio as a metric for construct quality (FIG. 3). This finding was reinforced by a physiological basis for said use wherein the differentiation of MSCs into osteoblasts is accompanied by a shift in metabolism (as described above). Further analysis of the correlation between the osteo-maturation markers (ALP activity and calcium deposition) and OUR/GCR revealed the existence of a threshold value in OUR/GCR of approximately 2.0 mol $O_2$/mol glucose. Values above 2.0 mol $O_2$/mol glucose correspond to mature/differentiating BTE constructs whereas values below 2.0 mol $O_2$/mol glucose correspond to immature/undifferentiated constructs (FIG. 4).

Beyond the degree of maturation, the cellularity of a BTE construct is another aspect of its quality. As such, a good quality monitoring methodology must be able to estimate a construct's cellularity non-destructively as well. Although rates of oxygen, glucose, and other metabolites have been used previously by many labs to predict cellularity non-destructively, these analyses have only been employed for non-differentiating cells with unchanging metabolic profile. In order to accommodate shifting metabolic profiles, the approach employed herein was to develop correlations for the cell-specific rates of oxygen uptake and glucose consumption as functions of OUR/GCR and use these alongside their construct-specific counterparts as a means to predict construct cellularity. Said correlations were determined to be well approximated by linear regressions (Eqns. 5 and 6). The resulting positive slope for the regression of $q_{O_2,avg}$ as a function of OUR/GCR demonstrates an increase in cellular oxygen uptake accompanying osteoblastic differentiation whereas the negative slope for that of $q_{glc,avg}$ as a function of OUR/GCR demonstrates a decrease in cellular glucose consumption accompanying said differentiation. These together suggest a metabolic shift as the immature MSCs, exhibiting a glycolytically-dominated metabolism, differentiate into osteoblasts benefiting more from oxidative phosphorylation for energy production.

Utilizing the regressions derived for the cell-specific oxygen uptake and glucose consumption rates along with their construct-specific rate counterparts, the cellularity of constructs was able to be determined (Eqns. 7 and 8). Comparison of these predicted values with those determined experimentally revealed the predictive capability of such approach (exhibiting $r^2$ values near 0.80). Furthermore, good confidence in said predicted values was observed (to within 20% of the experimentally-determined values). The implications of these results suggest that simple measurement of the oxygen uptake and glucose consumption rates of each construct can be used to determine the cellularity thereof during differentiation and maturation, a method previously unreported in the literature.

The presently disclosed results demonstrate the ability of a simple means for the real-time, non-destructive monitoring of both the cellularity and maturation (including differentiation and mineralization) of bone tissue engineered constructs cultured in vitro based on the measurement of macro-scale oxygen and glucose concentrations. The use of the ratio of the construct-specific rates of oxygen uptake and glucose consumption has been proposed as a viable method for such determination, and said use is supported on a physiological basis. Furthermore, monitoring of the production rates of osteoprotegerin and osteocalcin (as measured in circulating culture media) is comprises a supplementary method for the monitoring of early-stage (in the case of OPG) and late-stage (in the case of OCN) osteoblastic maturation of a construct. These metrics are easily implemented, and readily usable as a method of quality control and determination of optimal implant timing. The principles established herein could easily be adapted for the monitoring of tissue engineered constructs other than bone, such as cartilage, with the substitution of any of the markers utilized herein with those more relevant to the changing physio-metabolic profile of the cells of choice.

CITED REFERENCES

Alvarez-Barreto, J. F., S. M. Linehan, R. L. Shambaugh, and V. I. Sikavitsas. Flow Perfusion Improves Seeding of Tissue Engineering Scaffolds with Different Architectures. *Ann. Biomed. Eng.* 35:429-442, 2007.

Bancroft, G. N., V. I. Sikavitsas, and A. G. Mikos. Design of a Flow Perfusion Bioreactor System for Bone Tissue-Engineering Applications. *Tissue Eng.* 9:549-554, 2003.

Komarova, S. V., F. I. Ataullakhanov, and R. K. Globus. Bioenergetics and mitochondrial transmembrane potential during differentiation of cultured osteoblasts. *Am. J. Physiol.—Cell Physiol.* 279:C1220-C1229, 2000.

Pattappa, G., H. K. Heywood, J. D. de Bruijn, and D. A. Lee. The metabolism of human mesenchymal stem cells during proliferation and differentiation. *J. Cell. Physiol.* 226: 2562-2570, 2011.

dos Santos, F., P. Z. Andrade, J. S. Boura, M. M. Abecasis, C. L. da Silva, and J. M. S. Cabral. Ex vivo expansion of human mesenchymal stem cells: A more effective cell proliferation kinetics and metabolism under hypoxia. *J. Cell. Physiol.* 223:27-35, 2010.

Schop, D., F. W. Janssen, L. D. S. van Rijn, H. Fernandes, R. M. Bloem, J. D. de Bruijn, and R. van Dijkhuizen-Radersma. Growth, Metabolism, and Growth Inhibitors of Mesenchymal Stem Cells. *Tissue Eng. Part A* 15:1877-1886, 2009.

What is claimed is:

1. A process for producing a bone construct, comprising:
   providing a perfusion bioreactor having an inlet and an outlet;
   providing the perfusion bioreactor with a seeded scaffold comprising a porous scaffold seeded with mesenchymal stem cells (MSCs);
   continuously perfusing the seeded scaffold with an osteogenic induction media (OIM);
   measuring dissolved oxygen content of the OIM at the inlet and at the outlet to determine an oxygen uptake rate (OUR) for the seeded scaffold;
   measuring glucose content of the OIM to determine a glucose consumption rate (GCR) for the seeded scaffold; and
   removing the seeded scaffold from the perfusion reactor as a bone construct after the ratio of the OUR to the GCR (OUR/GCR) reaches or exceeds a predetermined threshold OUR/GCR value.

2. The process of claim 1, further comprising measuring osteoprotegerin content of the OIM for determining an osteoprotegerin production rate of the seeded scaffold.

3. The process of claim 1, further comprising measuring osteocalcin content of the OIM for determining an osteocalcin production rate of the seeded scaffold.

4. The process of claim 1, wherein the scaffold is seeded with the MSCs after being placed within the perfusion bioreactor.

5. The process of claim 1, further comprising implanting the bone construct into a treatment site of a subject to be treated.

6. The process of claim 1, further comprising using the bone construct in a test assay.

7. The process of claim 1, wherein the perfusion bioreactor comprises a closed-loop perfusion flow system comprising a source container for the OIM, a pump to continuously provide the OIM to the seeded scaffold, and a temperature controlled chamber to pass the OIM through the seeded scaffold and to return the OIM to the source container.

8. The process of claim 1, wherein the predetermined threshold OUR/GCR value is determined by comparing a first OUR/GCR rate value obtained from a first bone construct incubated with a baseline media to a second OUR/GCR rate value obtained from a second bone construct incubated with the OIM media, and identifying the predetermined threshold OUR/GCR value as the point at which the first OUR/GCR rate value and the second OUR/GCR rate value diverge, wherein the divergence persists for a minimum of 2 days.

9. The process of claim 1, wherein the predetermined threshold OUR/GCR value is about 2.0.

10. A process for determining maturity of a bone construct, comprising:
    providing a perfusion bioreactor having an inlet and an outlet;
    providing the perfusion bioreactor with a seeded scaffold comprising a porous scaffold seeded with mesenchymal stem cells (MSCs);
    continuously perfusing the seeded scaffold with an osteogenic induction media (OIM);
    measuring dissolved oxygen content of the OIM at the inlet and at the outlet to determine an oxygen uptake rate (OUR) for the seeded scaffold;
    measuring glucose content of the OIM to determine a glucose consumption rate (GCR) for the seeded scaffold;
    determining that the seeded scaffold is not sufficiently mature to be removed from the perfusion reactor as a bone construct when the ratio of the OUR to the GCR (OUR/GCR) has been determined to be less than a predetermined threshold OUR/GCR; and
    continuing to perfuse the seeded scaffold at least until the OUR/GCR reaches or exceeds the predetermined threshold OUR/GCR value.

11. The process of claim 10, further comprising measuring osteoprotegerin content of the OIM for determining an osteoprotegerin production rate of the seeded scaffold.

12. The process of claim 10, further comprising measuring osteocalcin content of the OIM for determining an osteocalcin production rate of the seeded scaffold.

13. The process of claim 10, wherein the scaffold is seeded with the MSCs after being placed within the perfusion bioreactor.

14. The process of claim 10, wherein the perfusion bioreactor comprises a closed-loop perfusion flow system comprising a source container for the OIM, a pump to continuously provide the OIM to the seeded scaffold, and a temperature controlled chamber to pass the OIM through the seeded scaffold and to return the OIM to the source container.

15. The process of claim 10, wherein the predetermined threshold OUR/GCR value is determined by comparing a first OUR/GCR rate value obtained from a first bone construct incubated with a baseline media to a second OUR/GCR rate value obtained from a second bone construct incubated with the OIM media, and identifying the predetermined threshold OUR/GCR value as the point at which the first OUR/GCR rate value and the second OUR/GCR rate value diverge, wherein the divergence persists for a minimum of 2 days.

16. The process of claim 10, wherein the predetermined threshold OUR/GCR value is about 2.0.

* * * * *